(12) United States Patent
Jan et al.

(10) Patent No.: US 9,162,952 B2
(45) Date of Patent: Oct. 20, 2015

(54) PROCESS FOR PURIFYING PRODUCTS FROM COAL TAR

(71) Applicant: UOP LLC, Des Plaines, IL (US)

(72) Inventors: Deng-Yang Jan, Elk Grove Village, IL (US); Robert L. Bedard, McHenry, IL (US); John Q. Chen, Glenview, IL (US); Peter K. Coughlin, Mundelein, IL (US); Jayant K. Gorawara, Buffalo Grove, IL (US); James A. Johnson, Burr Ridge, IL (US); Gregory F. Maher, Aurora, IL (US); Dean E. Rende, Arlington Heights, IL (US); Vasant P. Thakkar, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/472,152

(22) Filed: Aug. 28, 2014

(65) Prior Publication Data

US 2015/0141708 A1    May 21, 2015

Related U.S. Application Data

(60) Provisional application No. 61/906,117, filed on Nov. 19, 2013.

(51) Int. Cl.
| | |
|---|---|
| C07C 37/82 | (2006.01) |
| C07C 37/00 | (2006.01) |
| C07C 7/10 | (2006.01) |
| C07C 7/12 | (2006.01) |
| C07C 7/00 | (2006.01) |
| C10G 1/04 | (2006.01) |

(52) U.S. Cl.
CPC ............... *C07C 37/82* (2013.01); *C07C 7/005* (2013.01); *C07C 7/10* (2013.01); *C07C 7/12* (2013.01); *C07C 37/007* (2013.01); *C10G 1/045* (2013.01)

(58) Field of Classification Search
None
See application file for complete search history.

(56) References Cited

U.S. PATENT DOCUMENTS

| | | | |
|---|---|---|---|
| 1,528,313 A | 3/1925 | Weindel | |
| 1,937,941 A | 12/1933 | Braun | |
| 1,939,591 A | 12/1933 | Henke | |
| 1,955,023 A | 4/1934 | Leverkusen et al. | |
| 2,321,036 A | 6/1943 | Luten, Jr. et al. | |
| 2,368,597 A | 1/1945 | Morris et al. | |
| 2,378,232 A | 6/1945 | Luten, Jr. et al. | |
| 3,116,341 A | 12/1963 | Sheppard et al. | |
| 3,583,900 A | 6/1971 | Gatsis | |
| 4,098,838 A | 7/1978 | Grigoleit et al. | |
| 4,125,452 A | 11/1978 | Effron | |
| 4,133,646 A | 1/1979 | Farcasiu et al. | |
| 4,236,030 A | 11/1980 | Selwitz et al. | |
| 4,275,246 A | 6/1981 | Greco | |
| 4,382,855 A | 5/1983 | Ward et al. | |
| 4,386,225 A * | 5/1983 | Neuzil | 568/758 |
| 4,827,050 A | 5/1989 | Peter et al. | |
| 5,149,887 A * | 9/1992 | Zinnen | 568/751 |
| 5,177,300 A * | 1/1993 | Kulprathipanja et al. | 585/828 |
| 7,888,537 B2 | 2/2011 | Schmidt et al. | |

OTHER PUBLICATIONS

Kodera et al., "Methanol-Mediated Extraction Process for the Separation . . . ," Fuel (1993), 72(1), 57-58.
Bizek et al., "Extraction of Phenols: II. Distribution Data for Binary . . . ," Canadian Journal of Chemical Engineering (1993), 71(2), 256-263.
Scheibel et al., "Extraction of Solvent-Refined Coal Liquids," Coal Processing Technology (1981), 7, 26-35.
Tiwari, K. K., "Recovery and Dealkylation of Tar Acids," Central Fuel Research Institute, Dhanbad, India, Fuel Science and Technology (1982), 1(2), 107-109.
Gao et al., "Study on Caustic Washing Process for Extracting Phenolics . . . ," Journal of China Coal Society (2009), 34(10), 1383-1387.
Ye et al., "Solid Phase Extraction for Enrichment of Coal Extracts . . . ," Journal of Taiyuan University of Technology (2010), 41(5), 661-665.
Greminger et al., "Extraction of phenols from coal conversion process condensate waters", Energy Research (1979), 4(19), 98 pages.

* cited by examiner

Primary Examiner — Brian J Davis

(57) ABSTRACT

A process for purifying at least one product from coal tar is described. The process involves separating a coal tar fraction having a boiling point in the range of about 180° C. to about 230° C. into an acidic portion and a non-acidic portion by contacting the fraction with a caustic compound. The acidic portion is separated into a cresol portion and a xylenol portion, and the non-acidic portion is separated into a naphthalene portion and a naphthalene co-boiler portion. The acidic portion and the non-acidic portions are separated by contacting with an adsorbent comprising small, discrete crystallites, the adsorbent having less than 10 wt % amorphous binder component. The various portions can be separated in a similar manner.

17 Claims, 1 Drawing Sheet

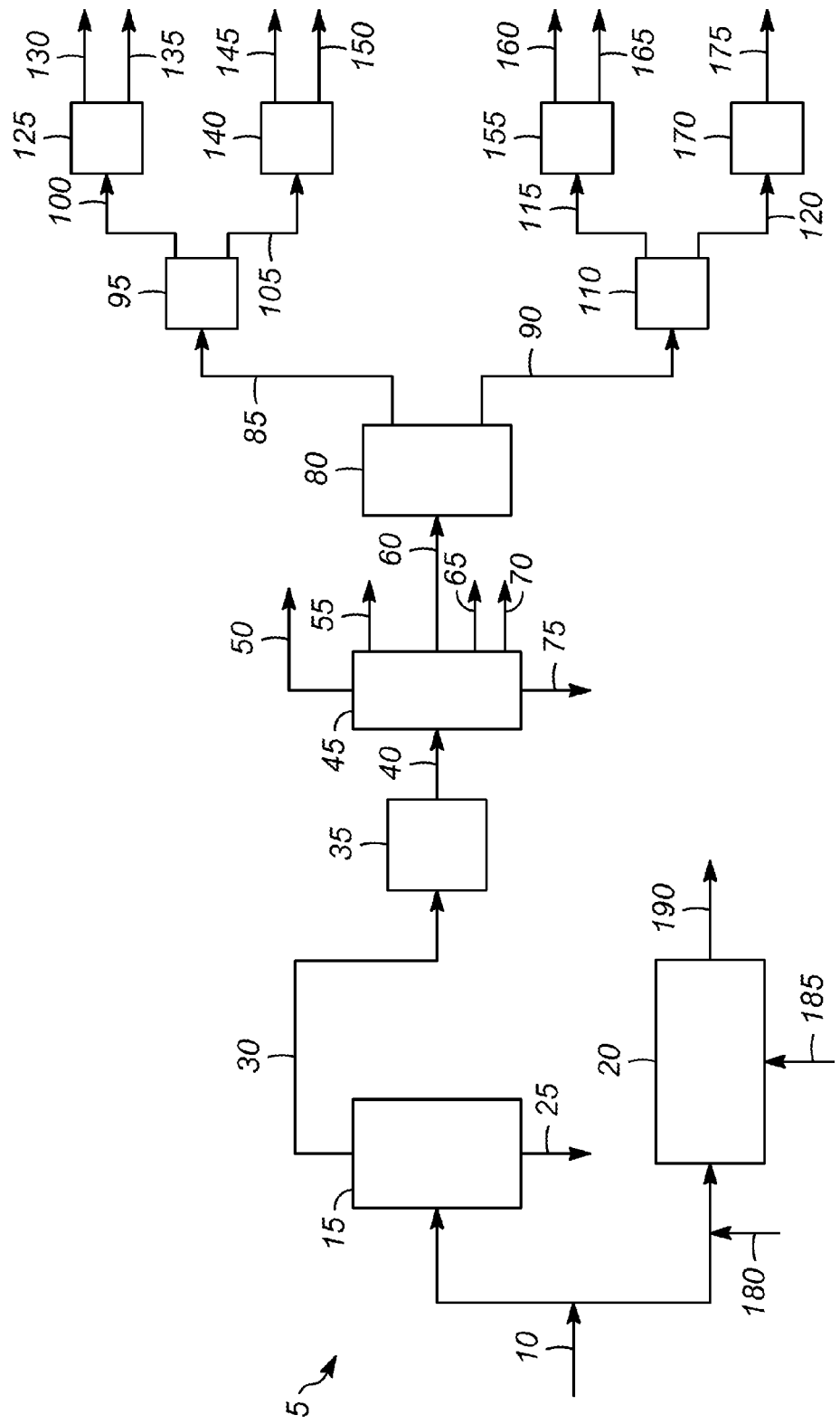

PROCESS FOR PURIFYING PRODUCTS FROM COAL TAR

This application claims the benefit of Provisional Application Ser. No. 61/906,117 filed Nov. 19, 2013, entitled Process for Purifying Products from Coal Tar.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which is used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains but may also be processed into fuels and petrochemical intermediates. The residual pitch left from the separation is used for paving, roofing, waterproofing, and insulation.

There is a need for improved processes for purifying products from coal tar.

SUMMARY OF THE INVENTION

One aspect of the invention is a process for purifying at least one product from coal tar. The process includes providing coal tar fraction having a boiling point in a range of about 180° C. to about 230° C. The coal tar fraction having the boiling point in the range of about 180° C. to about 230° C. is separated into an acidic portion and a non-acidic portion by contacting the fraction having the boiling point in the range of about 180° C. to about 230° C. with a caustic compound, the acidic portion comprising a mixture of phenols, cresols, and xylenols, and the non-acidic portion comprising naphthalenes and naphthalene coboilers. The acidic portion is separated into a cresol portion comprising a mixture of cresols and a xylenol portion comprising a mixture of xylenols by contacting the acidic portion with a cresol adsorbent comprising small, discrete crystallites, the cresol adsorbent having less than 10 wt % amorphous binder component, and desorbing the cresol portion from the cresol adsorbent with a cresol desorbent, or the non-acidic portion is separated into a naphthalene portion comprising aromatic hydrocarbons having two aromatic rings and a naphthalene co-boiler portion comprising aromatic hydrocarbons having one aromatic ring by contacting the non-acidic portion with a naphthalene adsorbent comprising small, discrete crystallites, the naphthalene adsorbent having less than 10 wt % amorphous binder component, and desorbing the naphthalene portion from the naphthalene adsorbent with a naphthalene desorbent, or both.

BRIEF DESCRIPTION OF THE DRAWING

The FIGURE is an illustration of one embodiment of the process of the present invention.

DETAILED DESCRIPTION OF THE INVENTION

The FIGURE shows one embodiment of a coal conversion process 5 of the present invention. The coal feed 10 can be sent to the pyrolysis zone 15, the gasification zone 20, or the coal feed 10 can be split into two parts and sent to both.

In the pyrolysis zone 15, the coal is heated at high temperature, e.g., up to about 2,000° C. (3600° F.) in the absence of oxygen to drive off the volatile components. Coking produces a coke stream 25 and a coal tar stream 30. The coke stream 25 can be used in other processes, such as the manufacture of steel.

The coal tar stream 30 which comprises the volatile components from the coking process can be sent to an optional contaminant removal zone 35, if desired.

The contaminant removal zone 35 for removing one or more contaminants from the coal tar stream or another process stream may be located at various positions along the process depending on the impact of the particular contaminant on the product or process and the reason for the contaminant's removal, as described further below. For example, the contaminant removal zone 35 can be positioned upstream of the separation zone 45, as shown in the FIGURE. Some contaminants have been identified to interfere with a downstream processing step or hydrocarbon conversion process, in which case the contaminant removal zone 35 may be positioned upstream of the separation zone 45 or between the separation zone 45 and the particular downstream processing step at issue. Still other contaminants have been identified that should be removed to meet particular product specifications. Where it is desired to remove multiple contaminants from the hydrocarbon or process stream, various contaminant removal zones may be positioned at different locations along the process. In still other approaches, a contaminant removal zone may overlap or be integrated with another process within the system, in which case the contaminant may be removed during another portion of the process, including, but not limited to the separation zone or the downstream hydrocarbon conversion zone. This may be accomplished with or without modification to these particular zones, reactors, or processes. While the contaminant removal zone is often positioned downstream of the hydrocarbon conversion reactor, it should be understood that the contaminant removal zone in accordance herewith may be positioned upstream of the separation zone, between the separation zone and the hydrocarbon conversion zone, or downstream of the hydrocarbon conversion zone or along other streams within the process stream, such as, for example, a carrier fluid stream, a fuel stream, an oxygen source stream, or any streams used in the systems and the processes described herein. The contaminant concentration is controlled by removing at least a portion of the contaminant from the coal tar stream 30. As used herein, the term removing may refer to actual removal, for example by adsorption, absorption, or membrane separation, or it may refer to conversion of the contaminant to a more tolerable compound, or both.

The viscosity of the coal tar stream can be reduced before it is separated in the separation zone using any suitable method, if desired. The viscosity can be reduced before or after the optional contaminant removal zone, for example. Suitable methods for reducing the viscosity of the coal tar stream include, but are not limited to, mixing the coal tar stream with a solvent (not shown).

The decontaminated coal tar stream 40 from the contaminant removal zone 35 is sent to a separation zone 45 where it is separated into two or more fractions. Coal tar comprises a complex mixture of heterocyclic aromatic compounds and their derivatives with a wide range of boiling points. The number of fractions and the components in the various fractions can be varied as is well known in the art. A typical separation process involves separating the coal tar into four to six streams. For example, there can be a fraction 50 comprising $NH_3$, CO, and light hydrocarbons, a light oil fraction 55 with boiling points between 0° C. and 180° C., a middle oil fraction 60 with boiling points between 180° C. to 230° C., a heavy oil fraction 65 with boiling points between 230 to 270° C., an anthracene oil fraction 70 with boiling points between 270° C. to 350° C., and a pitch fraction 75.

The light oil fraction contains compounds such as benzenes, toluenes, xylenes, naphtha, coumarone-indene, dicyclopentadiene, pyridine, and picolines. The middle oil fraction contains compounds such as phenols, cresols and cresylic acids, xylenols, naphthalene, high boiling tar acids, and high boiling tar bases. The heavy oil fraction contains benzene absorbing oil and creosotes. The anthracene oil fraction contains anthracene. Pitch is the residue of the coal tar distillation containing primarily aromatic hydrocarbons and heterocyclic compounds.

Suitable separation processes include, but are not limited to fractionation, solvent extraction, and adsorption.

Middle oil fraction 60 with boiling points between 180° C. to 230° C. is sent to separation zone 80 where it is contacted with a caustic compound using extraction media such as water, methanol, acetone or mixtures of the aforementioned at a combination of temperatures and pressures to operate in liquid phase. Suitable caustic compounds include, but are not limited to NaOH, KOH, and CaO. The middle oil fraction 60 is separated into an acidic portion 85 and a non-acidic portion 90. The acidic portion 85 comprises a mixture of phenols, cresols, and xylenols, while the non-acidic portion 90 comprises naphthalenes and naphthalene coboilers.

The acidic portion 85 is sent to cresol-xylenol separation zone 95 where it is contacted with a cresol adsorbent at temperatures ranging from about 100° C. to about 250° C. and pressures ranging from about 1.03 MPa (g) (150 psig) to about 6.89 MPa (g) (1000 psig). The acidic portion 85 is separated into a cresol portion 100 comprising a mixture of cresols and a xylenol portion 105 comprising a mixture of xylenols. The cresol portion is adsorbed by the cresol adsorbent. In order to recover the cresol portion, the cresol adsorbent is contacted with a cresol desorbent.

The phenols can be separated from the cresols and xylenols either by distillation of the acidic portion 85 before the cresol-xylenol separation or by distillation of the cresol portion 100 and the xylenol portion 105 after the cresol-xylenol separation (not shown).

The non-acidic portion 90 is sent to naphthalene separation zone 110 where it is contacted with a naphthalene adsorbent at temperatures ranging from about 100° C. to about 250° C. and pressures ranging from about 1.03 MPa (g) (150 psig) to about 6.89 MPa (g) (1000 psig). The non-acidic portion 90 is separated into a naphthalene portion 115 comprising a mixture of aromatic hydrocarbons having two aromatic rings and a naphthalene co-boiler portion 120 comprising a mixture of aromatic hydrocarbons having one aromatic ring. The naphthalene portion is adsorbed by the naphthalene adsorbent. In order to recover the naphthalene portion, the naphthalene adsorbent is contacted with a naphthalene desorbent.

The cresol adsorbent comprises small, discrete crystallites. The cresol adsorbent has less than 10 wt % of an amorphous binder component. In some embodiments, the small, discrete crystallites of the cresol adsorbent are less than about 1.8 μm. In some embodiments, the cresol adsorbent comprises Li—Na—K X-zeolite or Li—Na—K Y-zeolite. In some embodiments, the Li—Na—K X-zeolite or Li—Na—K Y-zeolite has a silica/alumina ($Si/Al_2$) molar ratio ranging from about 2.0 to about 6.0.

The naphthalene adsorbent comprises small, discrete crystallites. The naphthalene adsorbent has less than 10 wt % of an amorphous binder component. In some embodiments, the small, discrete crystallites of the naphthalene adsorbent are less than about 1.8 μm. In some embodiments, the naphthalene adsorbent comprises Li—Na X-zeolite or Li—Na Y-zeolite. In some embodiments, the naphthalene adsorbent comprises Li-containing X-zeolite. In some embodiments, the Li—Na X-zeolite or Li—Na Y-zeolite has a $Si/Al_2$ molar ratio of ranging from about 2.0 to about 6.0.

The cresol desorbent, the naphthalene desorbent, or both can comprise benzene, toluene, xylene, trimethylbenzene, indane, para-diethylbenzne (p-DEB), para-diisopropylbenzene (p-DIPB) or mixtures thereof. The cresol portion is separated from the cresol desorbent, or the naphthalene portion is separated from the naphthalene desorbent, or both, using known methods (not shown). Suitable desorbent separation methods include, but are not limited to, distillation and extraction.

The cresol portion 100 is sent to cresol separation zone 125 where it is contacted with a p-cresol adsorbent at temperatures ranging from about 100° C. to about 250° C. and pressures ranging from about 1.03 MPa (g) (150 psig) to about 6.89 MPa (g) (1000 psig). The cresol portion 100 is separated into a p-cresol portion 130 and a mixed cresol portion 135. The p-cresol portion 130 is adsorbed by the p-cresol adsorbent. In order to recover the p-cresol portion 130, the p-cresol adsorbent is contacted with a p-cresol desorbent.

The xylenol portion 105, which is typically rich in 2,6-xylenol, can be further purified by sending the xylenol portion 105 to xylenol separation zone 140 where it is contacted with a xylenol adsorbent at temperatures ranging from about 100° C. to about 250° C. and pressures ranging from about 1.03 MPa (g) (150 psig) to about 6.89 MPa (g) (1000 psig). The xylenol portion 105 is separated into a 2,6-xylenol portion 145 and a mixed xylenol portion 150. The 2,6-xylenol portion 145 is adsorbed by the xylenol adsorbent. In order to recover the 2,6-xylenol portion 145, the xylenol adsorbent is contacted with a xylenol desorbent.

The p-cresol adsorbent, the xylenol adsorbent, or both, comprises small, discrete crystallites. The cresol adsorbent, the xylenol adsorbent, or both, has less than 10 wt % of an amorphous binder component. In some embodiments, the small, discrete crystallites of the p-cresol adsorbent, the xylenol adsorbent, or both, are less than about 1.8 μm. In some embodiments, the p-cresol adsorbent, the xylenol adsorbent, or both comprise Na—K—Ba X-zeolite or Na—K—Ba Y-zeolite. In some embodiments, the Na—K—Ba X-zeolite or Na—K—Ba Y-zeolite or both has a $Si/Al_2$ molar ratio ranging from about 2.0 to about 6.0.

The p-cresol desorbent, the xylenol desorbent, or both, can comprise benzene, toluene, xylene, trimethylbenzene, indane, p-DEB, p-DIPB or mixtures thereof. The p-cresol portion 130 is separated from the cresol desorbent, or the 2,6-xylenol portion 145 is separated from the xylenol desorbent, or both, using known methods (not shown). Suitable desorbent separation methods include, but are not limited to, distillation and extraction.

The naphthalene portion 115 is sent to a dimethylnaphthalene separation zone 155 where it is contacted with a 2,6-dimethylnaphthalene adsorbent at temperatures ranging from about 100° C. to about 250° C. and pressures ranging from about 1.03 MPa (g) (150 psig) to about 6.89 MPa (g) (1000 psig). The naphthalene portion 115 is separated into a 2,6-dimethylnaphthalene portion 160 and a mixed unsubstituted and methyl-substituted naphthalene portion 165. The 2,6-dimethylnaphthalene portion 160 is adsorbed by the 2,6-dimethylnaphthalene adsorbent.

The 2,6-dimethylnaphthalene adsorbent comprises small, discrete crystallites. The 2,6-dimethylnaphthalene adsorbent has less than 10 wt % of an amorphous binder component. In some embodiments, the small, discrete crystallites of the 2,6-dimethylnaphthalene adsorbent are less than about 1.8 μm. In some embodiments, the 2,6-dimethylnaphthalene adsorbent comprises Li—Na X-zeolite or Li—Na Y-zeolite. In some embodiments, the 2,6-dimethylnaphthalene adsorbent comprises Na containing Y-zeolite. In some embodiments, the Li—Na X-zeolite, or the Li—Na Y-zeolite, or both, has a $Si/Al_2$ molar ratio ranging from about 2.0 to about 6.0.

In order to recover the 2,6-dimethylnaphthalene portion 160, the 2,6-dimethylnaphthalene adsorbent is contacted with a 2,6-dimethylnaphthalene desorbent. The 2,6-dimethylnaphthalene desorbent can comprise benzene, toluene, xylene, trimethylbenzene, indane, p-DEB, p-DIPB or mixtures thereof. The 2,6-dimethylnaphthalene portion 160 is then separated from the 2,6-dimethylnaphthalene desorbent using known methods (not shown). Suitable desorbent separation methods include, but are not limited to, distillation and extraction.

The naphthalene co-boiler portion 120 can be sent to a reaction zone 170. Some of the alkylbenzenes can be reacted to produce a product 175 containing phenolic functional groups. For example, the isopropyl functional group can be oxidized to the corresponding peroxide, followed by acid decomposition using $H_2SO_4$ or a solid acid to produce a phenolic functional group. For instance, methylpropylbenzene can be converted to methylphenol and acetone, and dimethylpropylbenzene can be converted to dimethylphenol (xylenol).

One or more of the fractions 50, 55, 65, 70, and 75 can be sent to one or more hydrocarbon conversion zones for further processing (not shown). Suitable hydrocarbon conversion zones include, but are not limited to, hydrotreating zones, hydrocracking zones fluid catalytic cracking zones, alkylation zones, transalkylation zones, oxidation zones and hydrogenation zones.

Hydrotreating is a process in which hydrogen gas is contacted with a hydrocarbon stream in the presence of suitable catalysts which are primarily active for the removal of heteroatoms, such as sulfur, nitrogen, oxygen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 27.6 MPa (4000 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

Hydrocracking is a process in which hydrocarbons crack in the presence of hydrogen to lower molecular weight hydrocarbons. Typical hydrocracking conditions may include a temperature of about 290° C. (550° F.) to about 468° C. (875° F.), a pressure of about 3.5 MPa (500 psig) to about 20.7 MPa (3000 psig), a liquid hourly space velocity (LHSV) of about 1.0 to less than about 2.5 $hr^{-1}$, and a hydrogen rate of about 421 to about 2,527 $Nm^3/m^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base.

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a powdered catalyst having the particles suspended in a rising flow of feed hydrocarbons to form a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPa g (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

Transalkylation is a chemical reaction resulting in transfer of an alkyl group from one organic compound to another. Catalysts, particularly zeolite catalysts, are often used to effect the reaction. If desired, the transalkylation catalyst may be metal stabilized using a noble metal or base metal, and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream comprising unconverted feed and product monoalkylated hydrocarbons. This effluent is normally cooled and passed to a stripping column in which substantially all C5 and lighter hydrocarbons present in the effluent are concentrated into an overhead stream and removed from the process. An aromatics-rich stream is recovered as net stripper bottoms, which is referred to as the transalkylation effluent.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour, weight hourly space velocity (WHSV), is generally in the range of from about 0.1 to about 30 $hr^{-1}$. The catalyst is typically selected to have relatively high stability at a high activity level.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutane alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7100 kPa absolute. The temperature range covered by this set of conditions is from about −20° C. to about 200° C. For at least alkylation of aromatic compounds, the volumetric ratio of hydrofluoric acid to the total amount of hydrocarbons entering the reactor should be maintained within the broad range of from about 0.2:1 to about 10:1, preferably from about 0.5:1 to about 2:1.

Oxidation involves the oxidation of hydrocarbons to oxygen-containing compounds, such as aldehydes. The hydrocarbons include alkanes, alkenes, typically with carbon numbers from 2 to 15, and alkyl aromatics, Linear, branched, and cyclic alkanes and alkenes can be used. Oxygenates that are not fully oxidized to ketones or carboxylic acids can also be subjected to oxidation processes, as well as sulfur compounds that contain —S—H moieties, thiophene rings, and sulfone groups. The process is carried out by placing an oxidation catalyst in a reaction zone and contacting the feed stream which contains the desired hydrocarbons with the catalyst in the presence of oxygen. The type of reactor which can be used is any type well known in the art such as fixed-bed, moving-bed, multi-tube, CSTR, fluidized bed, etc. The feed stream can be flowed over the catalyst bed either up-flow or down-flow in the liquid, vapor, or mixed phase. In the case of a fluidized-bed, the feed stream can be flowed co-current or counter-current. In a CSTR the feed stream can be continuously added or added batch-wise. The feed stream contains the desired oxidizable species along with oxygen. Oxygen can be introduced either as pure oxygen or as air, or as liquid phase oxidants including hydrogen peroxide, organic peroxides, or peroxy-acids. The molar ratio of oxygen ($O_2$) to substrate to be oxidized can range from about 5:1 to about 1:10. In addition to oxygen and alkane or alkene, the feed stream can also contain a diluent gas selected form nitrogen, neon, argon, helium, carbon dioxide, steam or mixtures thereof. As stated, the oxygen can be added as air which could also provide a diluent. The molar ratio of diluent gas to oxygen ranges from greater than zero to about 10:1. The catalyst and feed stream are reacted at oxidation conditions which include a temperature of about 25° C. to about 600° C., a pressure of about 101 kPa to about 5,066 kPa and a space velocity of about 100 to about 100,000 $hr^{-1}$.

Hydrogenation involves the addition of hydrogen to hydrogenatable hydrocarbon compounds. Alternatively hydrogen can be provided in a hydrogen-containing compound with ready available hydrogen, such as tetralin, alcohols, hydrogenated naphthalenes, and others via a transfer hydrogenation process with or without a catalyst. The hydrogenatable hydrocarbon compounds are introduced into a hydrogenation zone and contacted with a hydrogen-rich gaseous phase and a hydrogenation catalyst in order to hydrogenate at least a portion of the hydrogenatable hydrocarbon compounds. The catalytic hydrogenation zone may contain a fixed, ebulated or fluidized catalyst bed. Alternatively, the hydrogenation can be carried out in the liquid phase in a CSTR. This reaction zone is typically at a pressure from about 689 k Pa gauge (100 psig) to about 13790 k Pa gauge (2000 psig) with a maximum catalyst bed temperature in the range of about 177° C. (350° F.) to about 454° C. (850° F.). The liquid hourly space velocity is typically in the range from about 0.2 $hr^{-1}$ to about 10 $hr^{-1}$ and hydrogen circulation rates from about 200 standard cubic feet per barrel (SCFB) (35.6 $m^3$ /$m^3$) to about 10,000 SCFB (1778 $m^3$ /$m^3$).

In some processes, all or a portion of the coal feed 10 is mixed with oxygen 180 and steam 185 and reacted under heat and pressure in the gasification zone 20 to form syngas 190, which is a mixture of carbon monoxide and hydrogen. The syngas 190 can be further processed using the Fischer-Tropsch reaction to produce gasoline or using the water-gas shift reaction to produce more hydrogen.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for extracting at least one product from coal tar comprising:

providing a coal tar fraction having a boiling point in a range of about 180° C. to about 230° C.;

separating the coal tar fraction having the boiling point in the range of about 180° C. to about 230° C. into an acidic portion and a non-acidic portion by contacting the coal tar fraction having the boiling point in the range of about 180° C. to about 230° C. with a caustic compound, the acidic portion comprising a mixture of phenols, cresols, and xylenols, and the non-acidic portion comprising naphthalenes and naphthalene coboilers;

separating the acidic portion into a product cresol portion comprising a mixture of cresols and a product xylenol portion comprising a mixture of xylenols by contacting the acidic portion with a cresol adsorbent comprising discrete crystallites of less than 1.8 µm, the cresol adsorbent having less than 10 wt % amorphous binder component, and desorbing the product cresol portion from the cresol adsorbent with a cresol desorbent, or separating the non-acidic portion into a product naphthalene portion comprising aromatic hydrocarbons having two aromatic rings and a product naphthalene co-boiler portion comprising aromatic hydrocarbons having one aromatic ring by contacting the non-acidic portion with a naphthalene adsorbent comprising discrete crystallites of less than 1.8 µm, the naphthalene adsorbent having less than 10 wt % amorphous binder component, and desorbing the product naphthalene portion from the naphthalene adsorbent with a naphthalene desorbent, or both.

2. The process of claim 1 wherein the cresol desorbent, or the naphthalene desorbent, or both, comprises benzene, toluene, xylene, trimethylbenzene, indane, para-diethylbenzene, paradiisopropylbenzene, or mixtures thereof.

3. The process of claim 1 wherein the cresol adsorbent comprises Li—Na—K X-zeolite or Li—Na—K Y-zeolite.

4. The process of claim 3 wherein the Li—Na—K X-zeolite or Li—Na—K Y-zeolite has a silica to alumina (Si/Al$_2$) molar ratio from about 2.0 to about 6.0.

5. The process of claim 1 wherein the naphthalene adsorbent comprises Li—Na X-zeolite or Li—Na Y-zeolite.

6. The process of claim 1 further comprising one or more of:

separating the product cresol portion into a product p-cresol portion and a product mixed cresol portion by contacting the p-cresol portion with a cresol adsorbent comprising, discrete crystallites of less than 1.8 µm, the adsorbent having less than 10 wt % amorphous binder component, and desorbing the p-cresol portion with a p-cresol desorbent; or separating the product xylenol portion into a product 2,6-xylenol portion and a product mixed xylenol portion by contacting the xylenol portion with a xylenol adsorbent comprising, discrete crystallites of less than 1.8 µm, the xylenol adsorbent having less than 10 wt % amorphous binder component, and desorbing the product 2,6-xylenol portion with a xylenol desorbent; or separating the product naphthalene portion into a product 2,6-dimethylnaphthalene portion and a product mixed naphthalene portion by contacting the naphthalene portion with a 2,6-dimethylnaphthalene adsorbent comprising, discrete crystallites of less than 1.8 µm, the adsorbent having less than 10 wt % amorphous binder component, and desorbing the product 2,6-dimethylnaphthalene portion with a 2,6-dimethylnaphthalene desorbent.

7. The process of claim 6 wherein one or more of the p-cresol desorbent, or the xylenol desorbent, or the 2,6-dimethylnaphthalene desorbent comprises benzene, toluene, xylene, trimethylbenzene, indane, para-diethylbenzene, paradiisopropylbenzene, or mixtures thereof.

8. The process of claim 6 wherein the p-cresol adsorbent, or the xylenol adsorbent, or both, comprises Na—K—Ba X-zeolite or Na—K—Ba Y-zeolite.

9. The process of claim 8 wherein the Na—K—Ba X-zeolite or Na—K—Ba Y-zeolite has a silica to alumina (Si/Al$_2$) molar ratio ranging from about 2.0 to about 6.0.

10. The process of claim 6 wherein the 2,6-dimethylnaphthalene adsorbent comprises Li—Na X-zeolite or Li—Na Y-zeolite.

11. The process of claim 1 further comprising reacting at least a portion of the naphthalene co-boiler portion to form phenols.

12. A process for extracting at least one product from coal tar comprising:

a) pyrolyzing a coal feed into a coal tar stream and a coke stream;

b) separating the coal tar stream into at least two fractions, one of the fractions having a boiling point in a range of about 180° C. to about 230° C.;

c) separating the fraction having the boiling point in the range of about 180° C. to about 230° C. into an acidic portion and a non-acidic portion by contacting the fraction having the boiling point in the range of about 180° C. to about 230° C. with a caustic compound, the acidic portion comprising a mixture of phenols, cresols, and xylenols, and the non-acidic portion comprising naphthalenes and naphthalene coboilers;

d) separating the acidic portion into a product cresol portion comprising a mixture of cresols and a product xylenol portion comprising a mixture of xylenols by contacting the acidic portion with a cresol adsorbent comprising, discrete crystallites of less than 1.8 µm, the cresol adsorbent having less than 10 wt % amorphous binder component, and desorbing the product cresol portion from the cresol adsorbent with a cresol desorbent, or separating the non-acidic portion into a product naphthalene portion comprising aromatic hydrocarbons having two aromatic rings and a product naphthalene co-boiler portion comprising aromatic hydrocarbons having one aromatic ring by contacting the non-acidic portion with a naphthalene adsorbent comprising, discrete crystallites of less than 1.8 µm, the naphthalene adsorbent having less than 10 wt % amorphous binder component, and desorbing the product naphthalene portion from the naphthalene adsorbent with a naphthalene desorbent, or both;

and e) one or more of:

separating the product cresol portion into a product p-cresol portion and a product mixed cresol portion by contacting the cresol portion with a p-cresol adsorbent comprising, discrete crystallites of less than 1.8 µm, the adsorbent having less than 10 wt % amorphous binder component, and desorbing the product p-cresol portion with a cresol desorbent; or separating the product xylenol portion into a product 2,6-xylenol portion and product mixed xylenol portion by contacting the xylenol portion with a xylenol adsorbent comprising, discrete crystallites of less than 1.8 µm, the adsorbent having less than 10 wt % amorphous binder component, and desorbing the product 2,6-xylenol portion with a xylenol desorbent; or separating the product naphthalene portion into a product 2,6-dimethylnaphthalene portion and a product mixed naphthalene portion by contacting the naphthalene portion with a 2,6-dimethylnaphthalene adsorbent comprising, discrete crystallites of less than 1.8 μm, the 2,6-dimethylnaphthalene adsorbent having less than 10 wt % amorphous binder component, and desorbing the product 2,6-dimethylnaphthalene with a 2,6-dimethylnaphthalene desorbent.

13. The process of claim 12 wherein one of more of the cresol desorbent, the naphthalene desorbent, the p-cresol desorbent, the xylenol desorbent, or the 2,6-dimethylnaphthalene desorbent comprises benzene, toluene, xylene, trimethylbenzene, indane, para-diethylbenzene, paradiisopropylbenzene, or mixtures thereof.

14. The process of claim 12 wherein the cresol adsorbent comprises Li—Na—K X-zeolite or Li—Na—K Y-zeolite.

15. The process of claim 12 wherein the naphthalene adsorbent comprises Li—Na X-zeolite or Li—Na Y-zeolite.

16. The process of claim 12 wherein the p-cresol adsorbent, or the xylenol adsorbent, or both, comprises Na—K—Ba X-zeolite or Na—K—Ba Y-zeolite.

17. The process of claim 12 wherein the 2,6-dimethylnaphthalene adsorbent comprises Li—Na X-zeolite or Li—Na Y-zeolite.

* * * * *